US008652051B2

(12) United States Patent
Twery

(10) Patent No.: US 8,652,051 B2
(45) Date of Patent: Feb. 18, 2014

(54) CONTACT PRESSURE SENSING APPARATUS FOR USE WITH EXERCISE EQUIPMENT SENSORS

(75) Inventor: Sherwin Twery, Des Plaines, IL (US)

(73) Assignee: Brunswick Corporation, Lake Forest, IL (US)

(*) Notice: Subject to any disclaimer, the term of this patent is extended or adjusted under 35 U.S.C. 154(b) by 1308 days.

(21) Appl. No.: 11/696,404

(22) Filed: Apr. 4, 2007

(65) Prior Publication Data

US 2008/0249421 A1 Oct. 9, 2008

(51) Int. Cl.
*A61B 5/02* (2006.01)
(52) U.S. Cl.
USPC ............................ 600/481; 600/520
(58) Field of Classification Search
USPC ............ 600/481, 509, 520, 507, 513; 482/49; 128/898
See application file for complete search history.

(56) References Cited

U.S. PATENT DOCUMENTS

| | | | |
|---|---|---|---|
| 4,215,679 A | 8/1980 | Rustin | |
| 4,319,581 A | 3/1982 | Cutter | |
| 4,799,491 A * | 1/1989 | Eckerle | 600/485 |
| 5,365,934 A | 11/1994 | Leon et al. | |
| 5,372,365 A | 12/1994 | McTeigue et al. | |
| 5,524,637 A | 6/1996 | Erickson | |
| 5,585,785 A | 12/1996 | Gwin et al. | |
| 5,738,612 A | 4/1998 | Tsuda | |
| 5,772,601 A | 6/1998 | Oka et al. | |
| 5,906,581 A | 5/1999 | Tsuda | |
| 5,980,464 A | 11/1999 | Tsuda | |
| 6,018,677 A | 1/2000 | Vidrine et al. | |
| 6,165,129 A | 12/2000 | Bates | |
| 6,443,905 B1 * | 9/2002 | Nissila et al. | 600/490 |
| 6,656,126 B2 | 12/2003 | Starobin et al. | |
| 6,749,538 B2 * | 6/2004 | Slawinski et al. | 482/44 |
| 2003/0171190 A1 * | 9/2003 | Rice | 482/57 |
| 2004/0176226 A1 | 9/2004 | Carlson | |
| 2004/0209375 A1 * | 10/2004 | Diby et al. | 436/50 |
| 2005/0038348 A1 | 2/2005 | Avicola et al. | |
| 2005/0215340 A1 * | 9/2005 | Stites et al. | 473/233 |
| 2006/0047208 A1 | 3/2006 | Yoon | |
| 2008/0166028 A1 * | 7/2008 | Turek et al. | 382/124 |

* cited by examiner

*Primary Examiner* — Michael Kahelin
*Assistant Examiner* — Tho Tran
(74) *Attorney, Agent, or Firm* — Hanley, Flight & Zimmerman, LLC

(57) ABSTRACT

Contact pressure sensing apparatus for use with exercise equipment sensors are described. An example apparatus includes a sensor to detect a physiological condition of a user of an exercise device through physical contact with the user and a pressure sensor to detect a contact pressure applied by the user to the sensor.

22 Claims, 5 Drawing Sheets

CONTACT PRESSURE SENSING APPARATUS FOR USE WITH EXERCISE EQUIPMENT SENSORS

FIELD OF THE DISCLOSURE

The present disclosure relates to exercise equipment and, more particularly, to contact pressure sensing apparatus for use with exercise equipment sensors.

BACKGROUND

Exercise machines intended to provide a cardiovascular workout often include a sensor or sensors capable of detecting, measuring, or monitoring a physiological condition of a user. Displaying the information associated with the physiological condition allows the user to adjust the intensity of their workout (e.g., to achieve or maintain a target heart rate). More importantly, the information could serve as a precautionary measure for those with health or safety concerns. For example, a person with a medical condition or someone who is recovering from physical trauma may rely on the sensor to monitor their heart rate. Thus, accurate reading of a user's physiological condition (e.g., heart rate) and encouraging the user to utilize (e.g., grasp) the sensor(s) may be very important.

Detecting a physiological condition typically involves the placement of sensors on exercise equipment in locations at which a user is likely to make contact with the equipment. When grasped, the sensors detect a physiological signal (e.g. a pulse), which is then processed and analyzed. In some cases, the exercise machine automatically changes its operation (e.g., changes a speed or load) in response to the reading. In other cases, results (e.g., a heart rate) are merely displayed. However, in all cases, the sensors cannot acquire accurate information without sufficient contact with a user's skin. In other words, each sensor must make sufficient contact with the user's skin to accurately measure, detect, or monitor the physiological condition of the user. When a user's skin does not make sufficient contact with the sensors, the sensors may collect erroneous physiological information or no information at all.

While the most commonly used sensors employ metal electrodes, such electrodes have drawbacks. For example, perspiration from a user that is exercising is transferred to the electrode, making its surface difficult to grasp. Sustaining a grip in the proper location and with sufficient contact pressure on the electrode can be a considerable challenge, particularly as the user fatigues or loses focus on their grip. In particular, when a user's grip on the electrode and, thus, the contact pressure applied to the electrode is inefficient it could result in inaccurate physiological condition information (e.g., an erratic displayed heart rate), perhaps deterring a user from using the exercise machine or reducing the effectiveness of the exercise.

DETAILED DESCRIPTION

Figure 1:
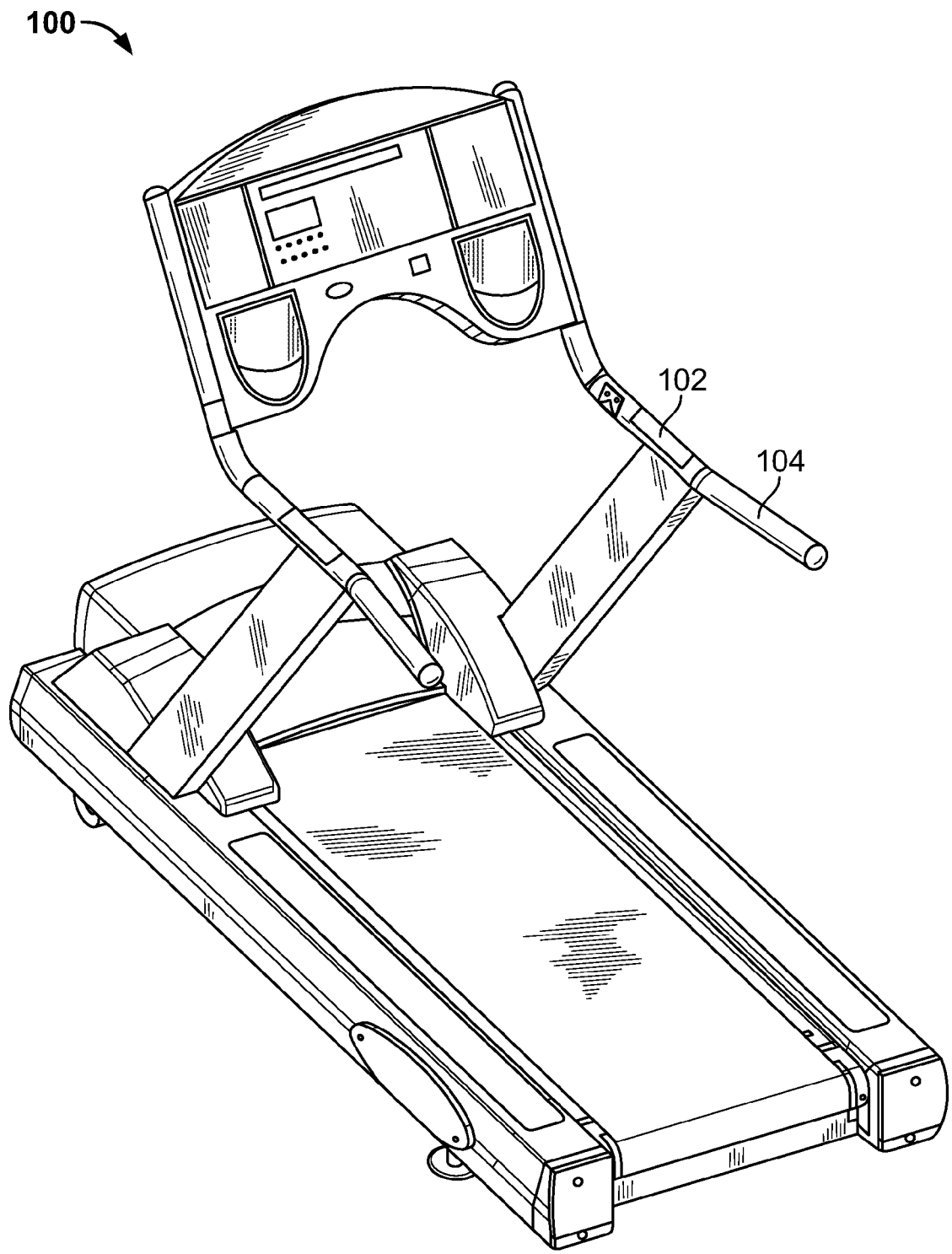
FIG. 1 is an example exercise machine that uses example pressure sensors to detect the contact pressure applied by a user to a sensor that detects a physiological condition.

FIG. 1 depicts an example exercise machine 100 that includes a sensor 102 to detect a physiological condition of a user and an example pressure sensor (described in connection with FIG. 2B). The example exercise machine 100 includes a frame 104 on which the sensor 102 and pressure sensor are mounted. During exercise, the user grips the frame 104 for assistance (e.g., to maintain balance or to rest) or as a preferred manner of performing the exercise. The sensor 102, along with the pressure sensor, may be placed in locations at which the user is likely to grasp the frame 104, thereby allowing the user to comfortably utilize the sensor 102. While FIG. 1 depicts the example exercise machine 100 as a treadmill, the sensor 102 and the pressure sensor described herein may be implemented on a variety of exercise machines (e.g., stationary bicycle exercise machines, recumbent bicycle exercise machines, stationary rowing machines, weight training machines, etc). Additionally, the sensor 102 and pressure sensor may be implemented in non-stationary apparatus including, for example, outdoor bicycles.

Figure 2A:
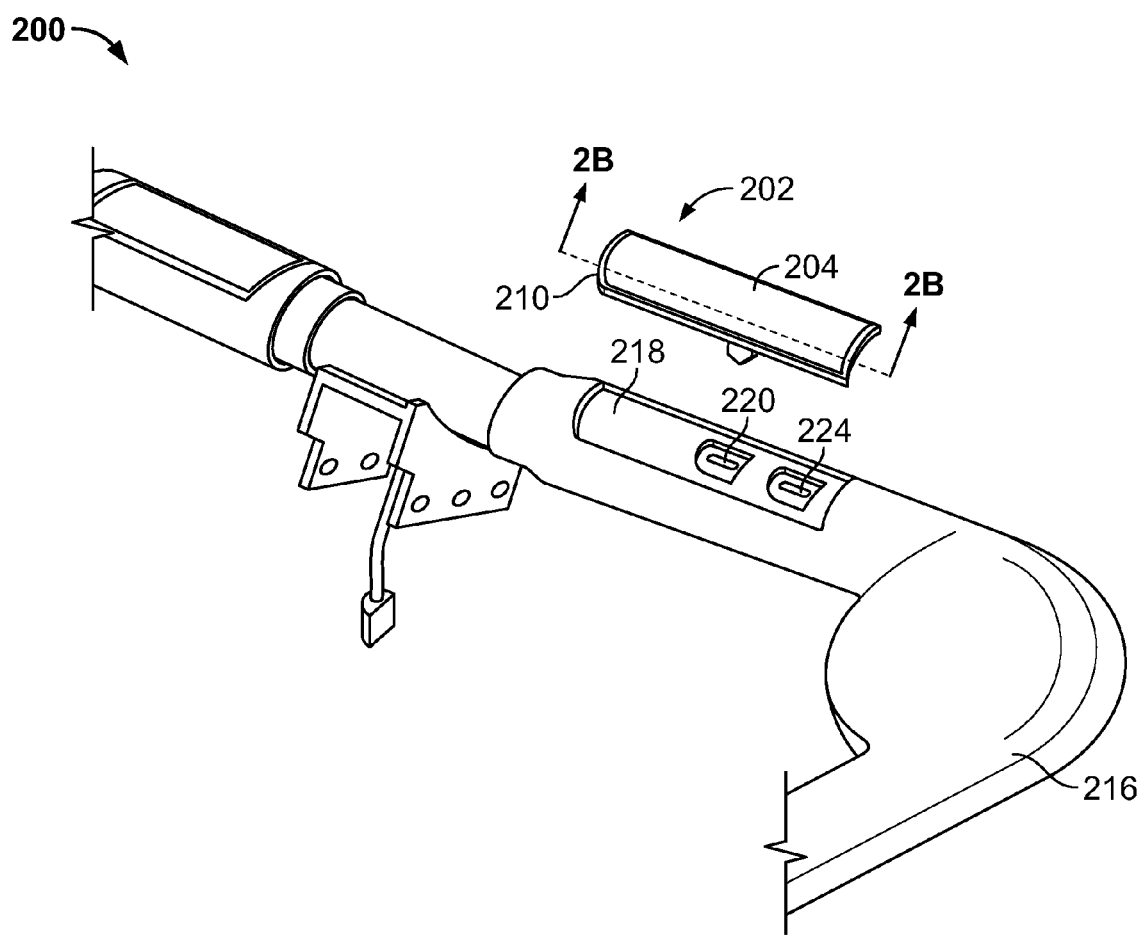
FIG. 2A illustrates an example portion of an exercise machine that uses an example pressure sensor to detect a contact pressure applied by a user to a sensor that detects a physiological condition.
Figure 2B:
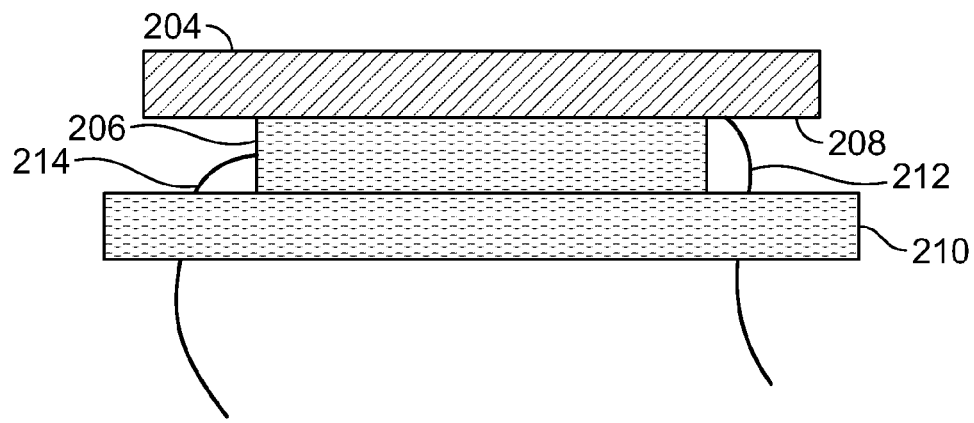
FIG. 2B is a cross-sectional view of the example sensor assembly shown in FIG. 2A.

FIGS. 2A and 2B illustrate an example frame portion 200 (e.g., a handlebar or other frame portion) of an exercise machine (e.g., the exercise machine 100 or any other exercise machine). The example frame portion 200 includes a sensor assembly 202 that includes a sensor 204 (e.g., an electrode) to measure, detect, or monitor a physiological condition (e.g., a heart rate) of a user. The sensor 204 detects physiological signals (e.g., electrical voltages or potentials) generated by a user through physical contact with the user's skin. The user must apply a sufficient contact pressure to (e.g., firmly grasp) the sensor 204 for it to operate properly.

To measure, detect, or monitor a physiological condition of a user, the sensor assembly 202 includes a pressure sensor 206 to detect or measure the contact pressure applied to the sensor 204 by a user. The pressure sensor 206 is engaged with or otherwise operatively coupled to the sensor 204 to enable the contact pressure applied to the sensor 204 to be detected or measured by the pressure sensor 206. For example, the pressure sensor 206 may be attached to an inner surface 208 of the sensor 204 using an adhesive, fasteners (e.g., clasps, clamps, etc.), or any other suitable method of attachment. Additionally or alternatively, the pressure sensor 206 may be mounted, along with the sensor 204, to a base or housing 210 (e.g., an open plastic casing molded and/or otherwise shaped or configured) to receive the sensor 204. As depicted in FIG. 2B, the pressure sensor 206 may be disposed between the sensor 204 and a housing 210 (e.g., by attaching the pressure sensor 206 to the inner surface 208 of the sensor 204), and mounted to the housing 210. The sensor 204 may be mounted or fixed to the housing 210 using any suitable methods (e.g., an adhesive or molding process). One or more apertures (not shown) may be provided in the housing 210 to enable signal lines 212 and 214 of the sensor 204 and the pressure sensor 206, respectively, to be routed through a frame member or support frame 216 to, for example, a processing system or unit (e.g., the processing unit 500 of FIG. 5).

The support frame 216 includes a recess 218 configured to receive the sensor assembly 202 and, in particular, the housing 210. The support frame 216 may include an aperture 220 in the recess 218 to provide access to a fastener or fastening assembly (e.g., nuts, bolts, etc.) that passes through the support frame 216. Additionally or alternatively, the housing 210 may be configured to snap into or to be press fit into the recess 218 and/or an adhesive could be used to affix the housing 210 to the recess 218 of the support frame 216. Further, the recess 218 of the support frame 216 may also include one or more apertures 224 to receive the signal lines or outputs 212 and 214 from the sensor 204 and the pressure sensor 206, respectively. The signal lines 212 and 214 are routed through the aperture(s) 224 and into the support frame 216 to, for example, a processing system or unit (e.g., the processing unit 500 of FIG. 5).

In operation, a user (e.g., a person using an exercise machine) may grasp the portion of the support frame 216 holding the sensor assembly 202. The pressure sensor 206 may then detect or measure an amount of contact pressure applied to the sensor 204 by the user. Once the contact pressure is obtained, the pressure sensor 206 may generate a corresponding electrical output signal (e.g., a voltage). The pressure sensor 206 can be implemented using any variety of sensor(s) capable of detecting or measuring an applied contact pressure by converting a force into an electrical signal. One such device is a strain gauge, which utilizes the deformation of a material (e.g., a metal foil) to measure a force (e.g., a contact pressure). When an object (e.g., a hand of a user of an exercise machine) directly or indirectly applies a force to the strain gauge, the force deforms the strain gauge material. The deformation results in a change in the electrical resistance of the material, which the strain gauge uses to generate a corresponding electrical signal. Other types of pressure or force sensors (e.g., variable capacitance sensors and/or piezoelectric sensors) capable of converting a mechanical force, such as a pressure applied by a person's hand, into an electrical output signal can be used.

The pressure sensor 206 is operatively coupled to circuitry that converts a varying resistance signal from the pressure sensor 206 (e.g., a resistance that varies in proportion to a pressure or force applied by a user to the pressure sensor 206 through the electrode or sensor 204) to a varying voltage signal. An example circuit 300 illustrated in FIG. 3 may be used to convert a varying resistance 302 generated by a pressure sensor (e.g., the pressure sensor 206 of FIG. 2B) to a corresponding voltage 304. A reference voltage 306 is applied to the varying resistance 302 (e.g., from the pressure sensor 206) to produce a control signal (i.e., the voltage 304). The reference signal 306 is amplified by an operational amplifier 308, commonly referred to as an op-amp, that is configured as an inverting gain stage. In particular, the reference signal 306 is coupled to the inverting terminal of the op-amp 308, and the non-inverting terminal of the op-amp is connected to a ground potential 309. The output of the op-amp 308 is connected to a negative feedback loop 310, which includes a potentiometer 312 and a fixed resistor 314 connected in series. Supplies 316 and 318 provide power to the op-amp 308.

Figure 3:
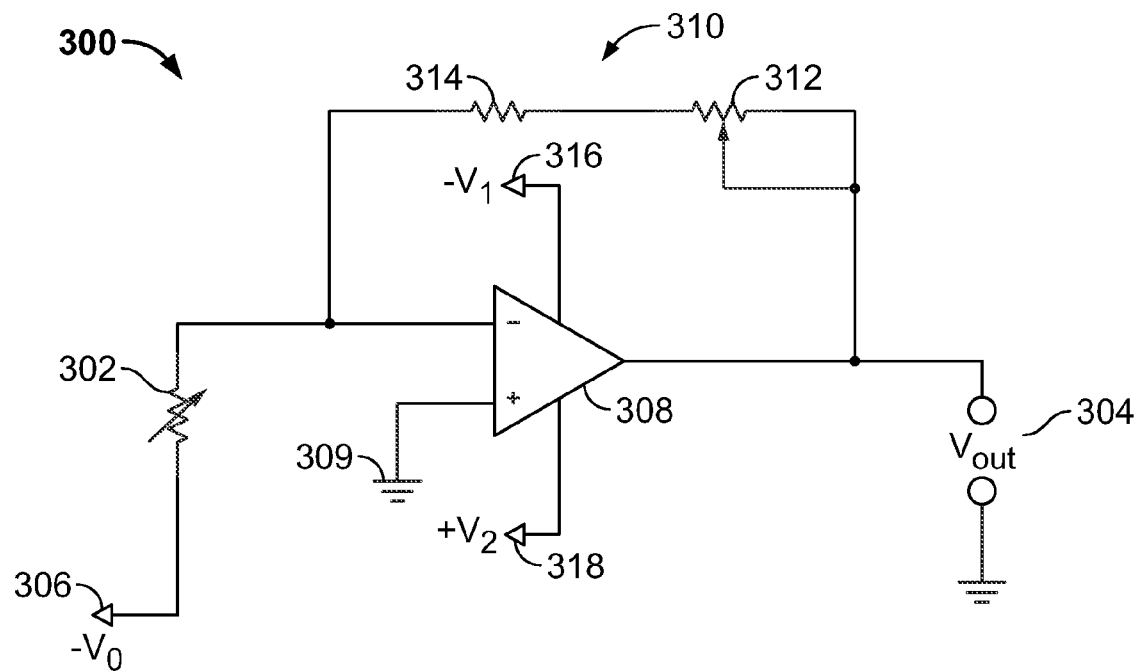
FIG. 3 illustrates a known circuit that may be used to process a variable resistance provided by the example pressure sensors described herein.

In operation, the output voltage 304 of the op-amp 308 is determined by the ratio of the variable resistance 302 generated by the pressure sensor 206 and the sum of the resistances 312 and 314. When the sensor 204 is contacted (e.g., by the hand of a user), a force is applied to the sensor 204 and, in turn, to the pressure sensor 206. The force applied to the pressure sensor 206 causes the variable resistance 302 to change (e.g., decrease), thereby causing the voltage 304 to change (e.g., increase). In this manner, the output voltage 304 varies in response to changes in the contact pressure a user's hand applies to the sensor 204. While FIG. 3 illustrates an example circuit 300 capable of converting a varying resistance 302 to a corresponding voltage 304, other circuits may be used to perform the conversion. Furthermore, alternative circuits may be used for alternative types of signals generated by the pressure sensor 206. For example, a pressure sensor may detect a force using a variable capacitance, in which case the circuit 300 of FIG. 3 would be modified to convert a varying capacitance to a varying output signal (e.g., a voltage or current).

The electrical signal (e.g., a varying voltage) generated via or in response to the pressure sensor 206 may be routed to a processing system or unit (e.g., the processing unit 500 discussed further below in connection with FIG. 5). The processing unit or system may communicate with a display (e.g., display 501 of FIG. 5) and may utilize the information associated with the pressure sensor 206 in any number of ways. The electrical signal may be interpreted to correspond to an amount of contact pressure applied at the sensor 204, which may be displayed, for example, numerically or graphically. Further, the processing unit or system may compare the contact pressure applied to the sensor 204 with a predetermined contact pressure threshold value and subsequently prompt the exerciser to change his or her grip pressure on the sensor 204 based on the comparison. The display may show the exerciser how close he or she may be to attaining the predetermined contact pressure or a predetermined desired applied contact pressure.

The sensor 204 (e.g., a metal electrode to detect a heart rate) requires a sufficient applied contact pressure to operate properly. Upon the detection of a physiological signal (e.g., a pulse from a person using an exercise machine), the sensor 204 generates a corresponding electrical output. However, the detection is usually performed in a noisy environment, as the human body produces many other signals corresponding to different bodily functions. For example, the contraction of muscles, which occurs frequently during exercise, produces a type of noise through which the heart rate is detected. Therefore, the initial or raw output of the sensor 204 is composed of multiple signals. To extract a desired physiological condition signal (e.g., a pulse signal), the initial output of the sensor 204 is processed further. In general, the output of the sensor 204 is filtered and amplified. One manner of processing the output of the sensor 204 is described in U.S. Pat. No. 5,365,934, which is incorporated herein by reference in its entirety.

Figure 5:
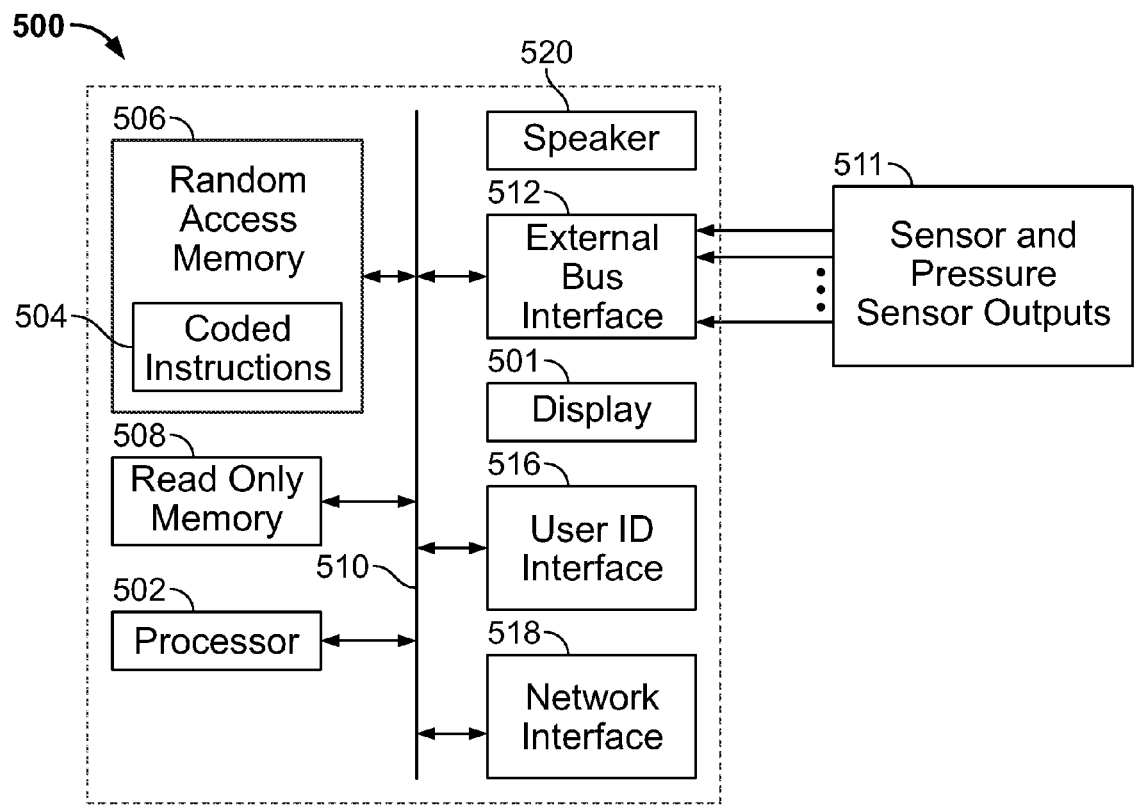
FIG. 5 illustrates an example manner of implementing an example processor and display unit.

Once the output from the sensor 204 is conditioned or processed, the resulting signal may be sent to a processing system or unit (e.g., the processing unit 500 of FIG. 5). Similar to the signal generated by the pressure sensor 206, the information associated with the sensor 204 may be utilized in a number of ways. The physiological information (e.g., a pulse or heart rate) may be displayed numerically or graphically. The exercise machine may automatically alter its operation (e.g., change a speed, load, or incline) based on the physiological information. Where the information associated with the sensor 204 includes a heart rate, a comparison may be made between the information generated by the sensor 204 and a predetermined target heart rate. Of course, any results from such operations may be displayed to the user.

While the sensor 204 and the pressure sensor 206 are capable of functioning independently, a processing system or unit (e.g., the processing unit 500 of FIG. 5) may facilitate an interaction between the two. For example, where the sensor 204 is configured to detect and display a heart rate, the result may be withheld from (e.g., not displayed to) the user unless a certain predetermined contact pressure threshold is detected or measured by the pressure sensor 206. This would prevent an exercise machine (e.g., the exercise machine 100 of FIG. 1) from displaying results that are likely to be inaccurate. Furthermore, while withholding the information associated with the sensor 204, the display unit could also show the difference between the predetermined contact pressure threshold and the actual contact pressure applied to the sensor 204. However, a user may have the option of disabling such restrictions. Another interaction may include a calculation of the accuracy of (e.g., a percentage representing a confidence in) the displayed information associated with the sensor 204 (e.g., a numerical heart rate) based on the information generated by the pressure sensor 206.

Figure 4:
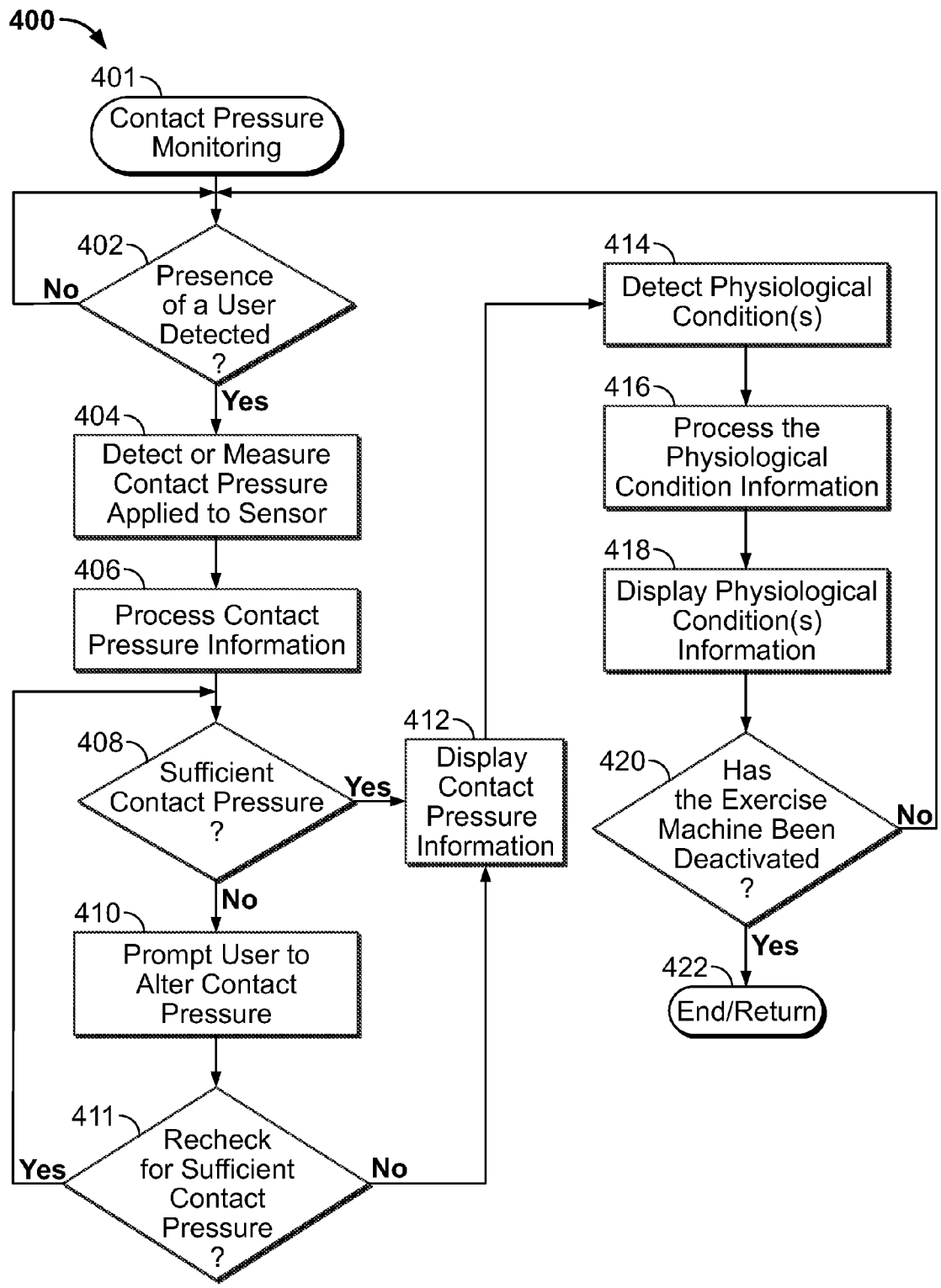
FIG. 4 is a flowchart representing an example process that may be performed by an exercise machine incorporating the example contact pressure sensing apparatus described herein.

FIG. 4 illustrates an example process 400 that may be performed by an exercise machine (e.g., the exercise machine 100 of FIG. 1) incorporating the example pressure sensor 206 of FIG. 2B. The process 400 commences when the exercise machine is activated. Such an exercise machine may be activated in a variety ways (e.g., pressing a button, moving a component, stepping onto the machine, etc.). In one example, once the exercise machine is activated, the sensor 204 and the pressure sensor 206 can begin receiving inputs. Next, the process 400 determines whether a user is present (block 402). For example, the process 400 may determine whether a user is utilizing (e.g., grasping) the sensor 204. The usage of the sensor 204 is detected when the pressure sensor 206 has an output indicating a change (e.g., a change in voltage or other electrical signal). In other words, the pressure sensor 206 detects that a user is present (i.e., using the sensor 204).

If a user is present, the pressure sensor 206 detects or measures the contact pressure applied to the sensor 204, as described above in connection with FIGS. 2A and 2B (block 404). The contact pressure information associated with or provided by the pressure sensor 206 is then processed (e.g., processed using the circuit 300 as described in connection with FIG. 3) (block 406). A processing system or unit (e.g., the processing unit 500 of FIG. 5) then determines whether the user is applying a sufficient contact pressure to the sensor 204 by, for example, determining if a predetermined contact pressure threshold is met (block 408). The contact pressure threshold may be established and stored on the exercise machine during manufacture, selected after assembly based on tests, or using other suitable methods. If the contact pressure threshold has not been met, the user is prompted to alter the contact pressure (block 410), after which the contact pressure may be rechecked against (e.g., compared to) the threshold (block 411). For example, the contact pressure may be rechecked a limited number of times or for a limited duration of time. The contact pressure information is displayed (e.g., numerically or graphically on a display or monitor) (block 412). If, at block 408, the contact pressure threshold has been met, the contact pressure information is displayed without prompting the user to alter the contact pressure (block 412).

The sensor 204 then measures, detects, or monitors the physiological signals generated by (and, thus, physiological condition(s) of) the user (block 414). As discussed above in connection with FIGS. 2A and 2B, the output from the sensor 204 then undergoes processing (e.g., filtration and amplification) to obtain a result (block 416). The resulting physiological condition information is then displayed (e.g., numerically or graphically on a display or monitor) to the user (block 418). This process is repeated until the exercise machine is deactivated (block 420). The example process 400 described above is only one example among many possible methods of operation. The operations described above may be reordered, rearranged, or performed simultaneously. Furthermore, as described above, signals from the sensor 204 and the contact pressure sensor 206 may interact or be processed together in alternative operations.

FIG. 5 is a schematic diagram of an example manner of implementing an example processor and display unit. To process and analyze the information generated by the sensors 204 and 206, the example processor and display unit 500 of FIG. 5 includes a general purpose programmable processor 502. The example processor 502 executes coded instructions 504 present in a main memory (e.g., within a random access memory (RAM) 506 as illustrated and/or within a read only memory (ROM) 508). The example processor 502 may be any type of processing unit, such as a microprocessor from the AMD®, Freescale® and/or Intel® families of microprocessors. The example processor 502 may execute, among other things, machine accessible instructions to perform the example process of FIG. 4 and/or the other processes described herein.

The example processor 502 is in communication with the example main memory (including the ROM 508 and the RAM 506) via a bus 510. The example RAM 506 may be implemented by dynamic random access memory (DRAM), Synchronous DRAM (SDRAM), and/or any other type of RAM device, and the example ROM 508 may be implemented by flash memory and/or any other desired type of memory device. Access to the example memories 508 and 506 may be controlled by a memory controller (not shown) in a conventional manner.

To receive sensor output signals 511, the example processor and display unit 500 includes any variety of conventional interface circuitry such as, for example, an external bus interface 512. For example, the external bus interface 512 may provide one input signal path (e.g., a semiconductor package pin) for each sensor. Additionally or alternatively, the external bus interface 512 may implement any variety of time multiplexed interface to receive output signals from the sensors via fewer input signals.

To display information for viewing by an exerciser or personal trainer, the example processor and display unit 500 includes any variety of display 501 (e.g., a liquid crystal display screen). To allow an exerciser to be identified, the example processor and display unit 500 includes any variety of user identification interface 516. Example interfaces 516 include a keypad, a radio frequency identification (RFID) tag reader, a universal serial bus (USB) memory interface, etc. For example, an exerciser may identify themselves by passing an associated device containing an RFID tag (e.g., a membership card) near an RFID tag reader 516. When the membership card is detected and/or identified by the RFID tag reader 516, the example RFID tag reader 516 provides to the example processor 502, for example, the exerciser's identification number (e.g., membership number) read and/or otherwise determined from the membership card.

To allow the example processor and display unit 500 to interact with a remote server, the example processor and display unit 500 includes any variety of network interfaces 518 such as, for example, a wireless LAN interface in accordance with, for instance, the Institute of Electronics and Electrical Engineers (IEEE) 802.11b, 802.11g, 802.15.4 (a.k.a. ZigBee) etc. standards. The example processor 502 may use the example network interface 518 to obtain target exercise parameters for an identified user and/or to provide exercise parameters determined while the identified user exercises.

To allow the example processor and display unit 500 to generate sounds, the example processor and display unit 500 includes any variety of speaker 520. The example processor 502 can cause any variety of sounds such as, for example, a user's current heart rate, to be produced by the example speaker 520 while a user is exercising.

Although an example processor and display unit 500 has been illustrated in FIG. 5, processor and display units may be implemented using any of a variety of other and/or additional devices, components, circuits, modules, etc. Further, the devices, components, circuits, modules, elements, etc. illustrated in FIG. 5 may be combined, re-arranged, eliminated and/or implemented in any of a variety of ways.

Figure 6:
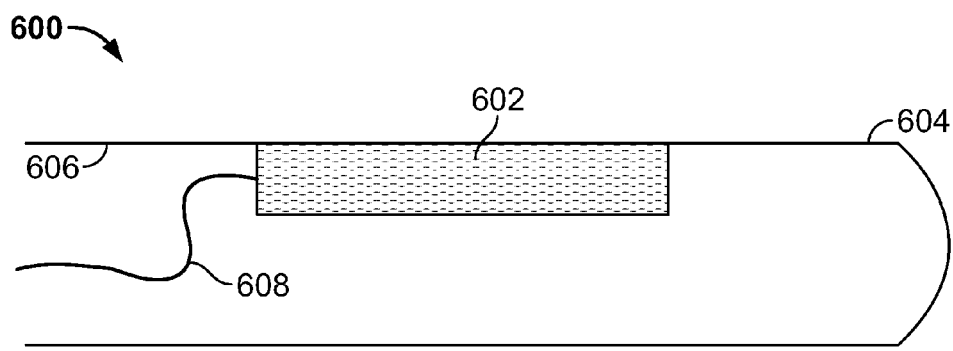
FIG. 6 is a cross-sectional view of an example portion of an exercise machine that uses an example pressure sensor to detect a contact pressure applied by a user to a support frame.

FIG. 6 depicts a portion of an example exercise machine 600 incorporating a pressure sensor 602. The pressure sensor 602 is integrated into a support frame 604 of an exercise machine, regardless of the presence of a sensor to detect a physiological condition (e.g., an electrode). The pressure sensor 602 may be attached (e.g., using an adhesive or a fastener) to an inside surface 606 of the support frame 604 to detect and/or measure a contact pressure applied to the support frame 604. The pressure sensor 602 may be placed in a location at which a user is likely to place his or her hands. The location may be designated (e.g., drawn symbols or stickers) on an outside surface of the support frame 604 to inform the user of the presence of the pressure sensor 602. Such a pressure sensor 602 operates similarly to the pressure sensor 206 described above in connection with FIGS. 2A and 2B. Rather than detecting and/or measuring the contact pressure applied to a sensor to detect a physiological condition (as in FIGS. 2A and 2B), the pressure sensor 602 in FIG. 6 detects and/or measures the contact pressure applied to the support frame 604 of an exercise machine. Any variety of pressure sensor(s) capable of converting a mechanical force into an electrical signal (as described in connection with FIG. 3) may be used. The electrical signal generated by the pressure sensor 602 is output via a signal line 608, which may be routed through the support frame 604 to a processing system or unit (e.g., the processing unit 500 of FIG. 5). The pressure sensor 602 may be used in conjunction with a processing system or unit (e.g., the processing unit 500 of FIG. 5) to detect if a user is present on an exercise machine, if a user is positioned properly on the exercise machine (e.g., to determine if they are using the machine properly), if a user is supporting too much of their body weight via their arms, or for any other suitable detection or measurement.

Although certain example methods and apparatus have been described herein, the scope of coverage of this patent is not limited thereto. On the contrary, this patent covers all methods and apparatus fairly falling within the scope of the appended claims either literally or under the doctrine of equivalents.

What is claimed is:

1. An apparatus for use with an exercise device, comprising:
   a physiological condition sensor to detect a physiological condition of a user of the exercise device through physical contact with the user;
   a pressure sensor to detect a contact pressure applied by the user to the physiological condition sensor; and
   a processor configured to compare the detected contact pressure with a threshold amount of pressure associated with an ability of the physiological condition sensor to detect the physiological condition, wherein the processor is configured to calculate a percentage representative of an accuracy of a reading of the physiological condition by the physiological condition sensor based on the comparison between the detected contact pressure and the threshold amount of pressure.

2. An apparatus as defined in claim 1, wherein the physiological condition is a heart rate.

3. An apparatus as defined in claim 1, wherein the physiological condition sensor to detect the physiological condition comprises an electrode.

4. An apparatus as defined in claim 1, wherein the pressure sensor is located between the physiological condition sensor and a frame of the exercise device.

5. An apparatus as defined in claim 1, wherein the processor is configured to cause the display to present the physiological condition.

6. An apparatus as defined in claim 1, wherein the processor is configured to cause a change in an operation of the exercise machine based on the physiological condition.

7. An apparatus as defined in claim 1, wherein the processor is configured to cause the display to present information associated with the contact pressure.

8. An apparatus as defined in claim 7, wherein the displayed information associated with the contact pressure comprises a difference between the detected contact pressure and the threshold amount of pressure.

9. An apparatus as defined in claim 1, wherein the processor is configured to cause presentation of an indication of how close the user is to attaining the threshold amount of pressure.

10. An apparatus as defined in claim 1, wherein the threshold amount of pressure is a non-zero value.

11. An apparatus as defined in claim 1, wherein the processor is configured to use the comparison to determine whether a sufficient amount of pressure is being applied by the user for the physiological condition sensor to accurately detect the physiological condition.

12. An apparatus as defined in claim 1, wherein the processor is configured to withhold a result of a reading of the physiological condition taken by the physiological condition sensor from the display based on the comparison of the detected contact pressure to the threshold amount of pressure.

13. An apparatus as defined in claim 1, wherein the processor is to cause a display to present an instruction to increase or decrease the contact pressure based on the comparison of the detected contact pressure and the threshold amount of pressure.

14. An apparatus as defined in claim 1, wherein the processor is configured to determine whether an excessive amount of weight of the user is being supported by arms of the user based on the detected contact pressure.

15. An apparatus for use with an exercise device, comprising:
   means for detecting a physiological condition of a user of the exercise device through physical contact with the user;
   means for detecting a contact pressure applied by the user to the means for detecting the physiological condition of the user; and
   means to compare the detected contact pressure with a threshold amount of pressure associated with an ability of the means for detecting the physiological condition to detect the physiological condition; and
   means to calculate a percentage representative of an accuracy of information generated by the means for detecting the physiological condition based on the comparison of the detected contact pressure to the threshold amount of pressure.

16. An apparatus as defined in claim 15, further comprising means to display a difference between the detected contact pressure and the threshold amount of pressure.

17. An apparatus as defined in claim 15, wherein the threshold amount of pressure is a non-zero value.

18. An apparatus as defined in claim 15, further comprising means to display an instruction to increase or decrease the contact pressure based on the comparison of the detected contact pressure and the threshold amount of pressure.

19. An apparatus for use with an exercise device, comprising:
- a physiological condition sensor to detect a physiological condition of a user of the exercise device through physical contact with the user;
- a pressure sensor to detect a contact pressure applied by the user to the physiological condition sensor;
- a display to present information related to the detected physiological condition; and
- a processor configured to compare the detected contact pressure with a threshold amount of pressure associated with an ability of the physiological condition sensor to detect the physiological condition, wherein the processor is configured to calculate an accuracy of the information displayed in connection with the physiological condition based on the comparison of the detected contact pressure to the threshold amount of pressure.

20. An apparatus as defined in claim 19, wherein the processor is configured to cause the display to present the user with a difference between the detected contact pressure and the threshold amount of pressure.

21. An apparatus as defined in claim 19, wherein the processor is configured to cause the display to present the user with an instruction to increase or decrease a grip pressure based on the comparison of the detected contact pressure and the threshold amount of pressure.

22. An apparatus as defined in claim 19, wherein the processor is configured to withhold a result of a reading of the physiological condition taken by the physiological condition sensor from a display based on the comparison of the detected contact pressure to the threshold amount of pressure.

* * * * *